United States Patent [19]

Koch

[11] Patent Number: 4,471,650

[45] Date of Patent: Sep. 18, 1984

[54] APPARATUS FOR TESTING CIGARETTES OR THE LIKE

[75] Inventor: Franz P. Koch, Schwarzenbek, Fed. Rep. of Germany

[73] Assignee: Hauni-Werke Körber & Co. KG., Hamburg, Fed. Rep. of Germany

[21] Appl. No.: 421,564

[22] Filed: Sep. 22, 1982

[30] Foreign Application Priority Data

May 14, 1982 [DE] Fed. Rep. of Germany ....... 3218163

[51] Int. Cl.³ ...................... G01N 15/08; G01M 3/04
[52] U.S. Cl. ........................................... 73/38; 73/41
[58] Field of Search ................ 73/38, 37, 41, 45, 45.1, 73/45.2

[56] References Cited

U.S. PATENT DOCUMENTS 3,948,084 4/1976 Heitmann et al. ...................... 73/41
4,223,551 9/1980 Greve et al. ............................ 73/38
4,403,501 9/1983 Pezzi ..................................... 73/38

Primary Examiner—S. Clement Swisher
Assistant Examiner—Joseph W. Roskos
Attorney, Agent, or Firm—Peter K. Kontler

[57] ABSTRACT

A cigarette testing apparatus wherein each end of the wrapper of a cigarette advancing with a rotary conveyor past a testing station receives a stream of gaseous testing fluid from a conduit which is connected with a source of testing fluid, and wherein a further conduit connects the interior of the wrapper at the testing station with an electropneumatic transducer which generates signals denoting the condition of successively tested wrappers. In order to prevent columns of testing fluid in the conduits from oscillating as a result of abrupt establishment and/or abrupt termination of communication between such conduits and the wrappers of cigarettes moving toward, past and beyond the testing station and from thereby distorting the signals which are generated by the transducer, at least one such conduit admits a stream of fluid into an oscillation-preventing device having an injector nozzle serving to convert the inflowing stream into a coherent laminar flow which traverses, without guidance, a chamber whose interior is maintained at atmospheric pressure, and which thereupon advances toward the testing station or toward the transducer by flowing through an intercepting orifice.

11 Claims, 2 Drawing Figures

APPARATUS FOR TESTING CIGARETTES OR THE LIKE

BACKGROUND OF THE INVENTION

The present invention relates to improvements in apparatus for testing cigarettes or analogous rod-shaped articles which constitute or form part of smokers'0 products. More particularly, the invention relates to improvements in apparatus for testing cigarettes or analogous rod-shaped articles (hereinafter referred to as cigarettes) during transport by a rapidly advancing conveyor, such as a rotary drum-shaped conveyor which rotates about its axis and is provided with peripheral flutes or analogous receiving means wherein the cigarettes are held in parallelism with the axis of the conveyor during travel toward, through or past and beyond a testing station.

It is known to test cigarettes or analogous rod-shaped articles of the tobacco processing industry by causing streams of air or another gaseous testing fluid to flow radially through the wrappers of successive cigarettes and by monitoring the pressure differential between the interior and the exterior of the wrappers. It is also known to test the wrappers of cigarettes for integrity by monitoring the pressure of testing fluid which is admitted into one end of the wrapper, by monitoring the pressure of fluid (if any) which issues from the other end of the wrapper, and by ascertaining the differential between the pressures of the inflowing and outflowing fluids. The testing fluid can be caused to flow through the wrappers of successive cigarettes by suction, or at least one end of the wrapper of the cigarette at the testing station can be connected with a source of compressed gaseous testing fluid.

As a rule, the wrappers of cigarettes are tested in the manufacturing machine itself or in a machine which processes the cigarettes, for example, in a filter tipping machine wherein plain cigarettes are joined with filter mouthpieces to form therewith filter cigarettes of unit length or multiple unit length. The testing can involve attempts at detection of open seams, holes, frayed ends of the wrappers, a combination of such defects and/or a monitoring of the porosity of intentionally perforated portions of the wrappers of plain cigarettes or filter cigarettes, namely, of wrapper portions which are perforated for the purpose of admitting relatively cool atmospheric air into the column of hot tobacco smoke. Many manufacturers of cigarettes demand the utilization of perforated wrappers because they believe that the admission of cool atmospheric air exerts a beneficial influence upon and reduces the presumably deleterious effects of tobacco smoke upon the health of the smoker. In many instances, the testing operation involves admission of compressed testing fluid (normally air) into both ends of a cigarette and monitoring the drop of pressure (if any) which develops as a result of escape of some testing fluid through the wrapper of the tested article. The differential between the pressure of the admitted testing fluid and the pressure of testing fluid in the interior of the wrapper of a cigarette at the testing station is indicative of the quality or condition of the tested article. The signals which are generated to denote the detected pressure differential are evaluated and, if warranted, utilized to segregate defective articles from satisfactory articles prior to entry of defective articles into the next machine, such as a packing machine which normally follows a filter tipping machine. The testing of filter cigarettes in a filter tipping machine is further indicative of the condition of the uniting band which is utilized to couple the filter mouthpiece with the tobacco-containing portion, e.g., with a plain cigarette. If the sealing action of the uniting band is unsatisfactory, excessive quantities of testing fluid will escape in the region where the plain cigarette abuts against the adjacent end portion of the filter.

Cigarettes are tested while advancing at the operating speed of a making or processing machine. The output of such machines is extremely high; for example, a modern filter tipping machine can turn out well in excess of one-hundred filter cigarettes per second. Therefore, the intervals which are allotted for the testing of individual cigarettes in a filter tipping or an analogous machine are extremely short, normally in the range of a few milliseconds. During such extremely short intervals, the pressure of testing fluid which is admitted into the interior of a cigarette at the testing station must be built up at both ends of the cigarette, and the signal denoting the drop of pressure as a result of porosity or defectiveness of the wrapper must be generated within the same short interval of time, namely, before the pressure of testing fluid is reduced again and not later than when the freshly tested cigarette advances beyond the testing station.

Each application and termination of pressure of testing fluid entails oscillations of the column of testing fluid in the form of standing waves in the conduits for testing fluid. Such oscillations of testing fluid are highly likely to distort the results of the testing operation. Therefore, the testing of a preceding cigarette must be followed by an interval which is long enough to allow the oscillations to fade out, i.e., the column of testing fluid in the conduit or conduits leading to and from the testing station must cease to oscillate before the transducer which converts pneumatic signals into electrical or other suitable signals for further processing generates a signal denoting the condition of the tested article. This entails considerable shortening on the aforediscussed extremely short intervals of time which are available for the testing of successive cigarettes during transport through the testing station in a modern high-speed cigarette making or processing machine. The shorter the intervals which are available for actual testing, the greater is the likelihood of distortion of signals which denote the condition of the tested articles. Furthermore, the aforediscussed shortening of extremely short intervals which are available for testing of successive cigarettes, namely, a shortening for the purpose of permitting the oscillations of testing fluid to disappear, reduces the possibility of further increasing the output of the machines in which the testing apparatus are used. In other words, if all other units of a machine for the making or processing of cigarettes would allow a pronounced increase of the output, for example, to 10,000 cigarettes per minute, presently known testing apparatus would prevent such increase in output because their operation at corresponding speeds of the articles to be tested would be unsatisfactory so that they would permit defective cigarettes to reach the next processing station and/or would or could cause ejection or segregation of satisfactory cigarettes.

OBJECTS AND SUMMARY OF THE INVENTION

An object of the invention is to provide a testing apparatus for cigarettes or the like wherein the entire interval of dwell of a rapidly advancing article at the testing station can be utilized for actual determination of the condition of such article.

Another object of the invention is to provide a testing apparatus which can properly test the wrappers and/or other constituents of cigarettes or analogous rod-shaped articles in a cigarette making or filter tipping machine, even if the speed of the machine is increased beyond the speed at which presently known testing apparatus can reliably test successive articles.

A further object of the invention is to provide a testing apparatus which can be installed in existing cigarette making, filter tipping or analogous machines as a superior substitute for presently known testing apparatus.

Another object of the invention is to provide a testing apparatus which eliminates oscillations of the column or columns of testing fluid in a simple, inexpensive and space-saving manner.

An additional object of the invention is to provide the testing apparatus with novel and improved means for admitting testing fluid into the wrappers of successive cigarettes or analogous smokers' articles.

A further object of the invention is to provide a novel and improved method of preventing oscillations of columns of testing fluid in conduits which admit testing fluid to the wrappers of cigarettes or analogous rod-shaped articles during transport of the articles through the testing station.

An additional object of the invention is to provide a testing apparatus which is more accurate and more reliable than heretofore known testing apparatus, even if the rate at which the articles to be tested are transported therethrough greatly exceeds the speed of transported articles in conventional testing apparatus.

An additional object of the invention is to provide the testing apparatus with novel and improved means for regulating the flow of testing fluid between a source of testing fluid and one or both ends of an article at the testing station.

The improved testing apparatus is utilized to test, at a testing station, the open-ended tubular wrappers of cigarettes or analogous rod-shaped articles wherein the wrapper surrounds a filler consisting of tobacco and/or filter material. The apparatus comprises conveyor means (e.g., a rotary drum-shaped conveyor having axially parallel peripheral article-receiving flutes) arranged to transport a succession of articles toward, past and beyond the testing station (preferably in such a way that the articles are transported sideways, i.e., at right angles to their respective axes), and means for admitting a stream of gaseous testing fluid (e.g., air) into at least one end of the wrapper forming part of the article advancing past the testing station with attendant establishment of a pressure differential between the interior and the exterior of the wrapper. Such fluid admitting means includes a source of preferably compressed gaseous testing fluid, conduit means for conveying testing fluid between the source and the testing station (i.e., from the source toward the testing station if the testing fluid is maintained at superatmospheric pressure), and means for preventing oscillations of testing fluid in the conduit means as a result of abrupt admission and/or abrupt termination of admission of testing fluid into the wrappers of articles at the testing station. The oscillation preventing means comprises an injector nozzle receiving the stream of testing fluid from the conduit means and being designed to convert the stream into a coherent jet or flow, means defining an intercepting orifice located in the path of the coherent flow and serving to convey the flow to the testing station, and means defining a chamber which communicates with the atmosphere and through which the coherent flow advances with clearance on its way from the injector nozzle into the orifice. The testing apparatus further comprises an electropneumatic transducer or other suitable signal generating means for monitoring the aforementioned pressure differential between the interior and the exterior of the wrapper at the testing station.

The diameter of the chamber exceeds the diameter of the outlet end of the passage which is defined by the injector nozzle and also the diameter of the intercepting orifice, i.e., the coherent flow traverses the chamber without any guidance during propagation from the nozzle toward and into the intercepting orifice.

The orifice defining means can comprise a stationary valve member which preferably supports the nozzle as well as the chamber defining means and is adjacent to one end of the wrapper at the testing station. Such valve member is formed with a suitably configurated groove or analogous means for admitting testing fluid into the adjacent end of the wrapper while the respective article advances past the testing station.

The diameter of the inlet portion of the passage which is defined by the injector nozzle preferably diminishes in a direction from the conduit means toward the chamber, and the length of the passage which is defined by the injector nozzle is preferably selected in such a way that the flow issuing from the nozzle is a laminar flow which is free of turbulence.

The apparatus can comprise second conduit means which also receives a stream of testing fluid from the aforementioned source and serves to convey such fluid toward the other end of the wrapper which advances past the testing station. Such apparatus can comprise second oscillation preventing means which is interposed between the second conduit means and the testing station to prevent oscillations of testing fluid in the second conduit means.

Still further, the apparatus can comprise additional conduit means which conveys testing fluid between the interior of a wrapper at the testing station and the monitoring means or which conveys to the monitoring means testing fluid whose pressure has been influenced by the condition of the wrapper at the testing station. Such apparatus can comprise additional oscillation preventing means which is associated with the additional conduit means.

The injector nozzle can be mounted in such a way that it is coaxial with the chamber defining means, with the orifice defining means as well as with the wrapper at the testing station.

The novel features which are considered as characteristic of the invention are set forth in particular in the appended claims. The improved testing apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
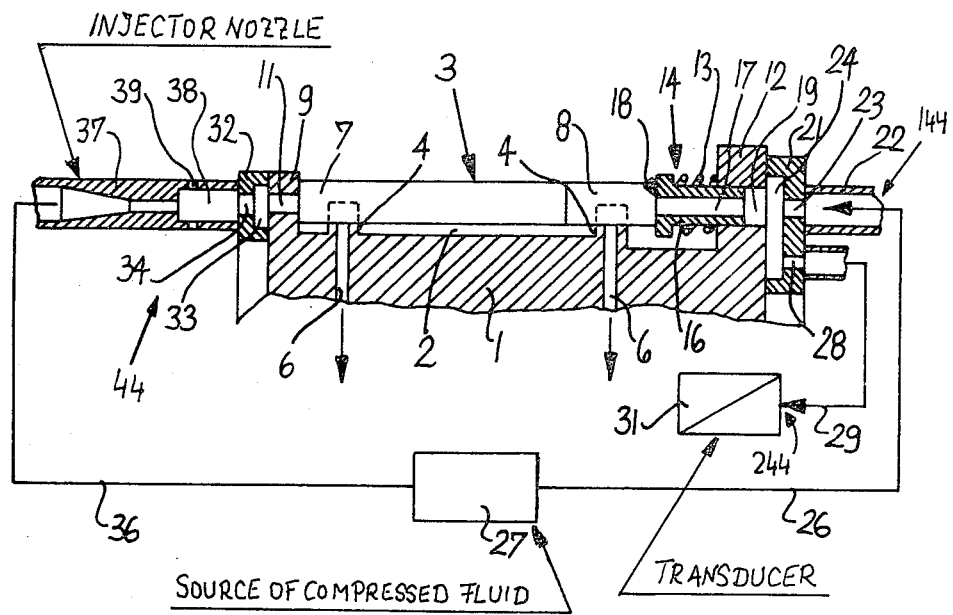
FIG. 1 is a fragmentary partly diagrammatic and partly axial sectional view of a testing apparatus wherein the development of oscillations in the column or columns of testing fluid is prevented or reduced in accordance with the present invention.

Referring first to FIG. 1 there is shown a portion of a testing apparatus for filter cigarettes 3 each of which includes an elongated tobacco-containing portion or plain cigarette 7 and a filter 8 which is connected to the right-hand end portion of the plain cigarette 7 by a uniting band, not specifically shown. The cigarette 3 is held in an axially parallel peripheral flute 2 of a rotary drum-shaped testing conveyor 1 which rotates about an axis extending in parallism with the axis on the cigarette 3. The means for driving the conveyor 1 at the speed of other moving parts in a filter tipping machine is not specifically shown in the drawing. Reference may be had to commonly owned U.S. Pat. No. 3,948,084 granted Apr. 6, 1976 to Heitmann et al. The disclosure of this patent is incorporated herein by reference. The machine in which the testing apparatus of the present invention is installed can be a machine of the type known as MAX-S manufactured and sold by the assignee of the present invention. Machines of such type are described, for example, in commonly owned U.S. Pat. No. 4,281,670 granted Aug. 4, 1981 to Heitmann et al. The disclosure of this patent is also incorporated herein by reference.

The periphery of the testing conveyor 1 has several equidistant flutes 2 each of which can carry a discrete cigarette 3 toward, past and beyond the testing station which is shown in the upper part of FIG. 1. Each flute 2 contains two raised portions or projections 4 having small end faces one of which is in contact with the wrapper of the respective plain cigarette 7 and the other of which is in contact with the wrapper of the respective filter 8. The projections 4 are formed with suction ports 6 which are connected with a suction generating device (not specifically shown) so as to ensure that the cigarettes 3 are held in their flutes 2 during transport toward, past and beyond the testing station. Such cigarettes are admitted into the respective flutes 2 by a cigarette feeding conveyor at one side of the testing station, and successive tested cigarettes are removed from their flutes 2 at the other side of the testing station to enter the flutes of a further conveyor, not shown. The area of contact between each projection 4 and the respective cigarette 3 is small or very small in order to ensure that such projections will not accidentally seal holes, portions of open seams or other types of defects in the wrappers of articles advancing past the testing station.

The left-hand end portion of the conveyor 1, as viewed in FIG. 1, is formed with a collar or flange 9 which extends radially outwardly beyond the adjacent projections 4 and is formed with axially parallel bore 11 the right-hand ends of which are sealed by the left-hand end faces of cigarettes 3 in the respective flutes 2. The right-hand end portion of the conveyor 1 is also formed with a radially outwardly extending collar or flange 12 having an annulus of axially parallel bores 19 each of which constitutes a socket for a reciprocable sealing nipple 14. Each socket 19 is in register with one of the bores 11 in the left-hand flange 9 of the conveyor 1. The illustrated nipple 14 is biased in a direction to the left, as viewed in FIG. 1, by a coil spring 13 which reacts against the flange 12 and bears against the larger-diameter left-end portion of the nipple. The end face 18 of the nipple 14 abuts against the adjacent cigarette 3 so that the right-hand end face of such cigarette seals the corresponding end of an axial passage or bore 17 in the nipple 14. The sleeve 16 of the nipple 14 is reciprocable, with negligible play, in the respective socket 19 of the flange 12. The nipple 14 is depressed into the socket 19 against the opposition of the coil spring 13 when the corresponding flute 2 is to discharge a freshly tested cigarette 3 and when such flute is to receive an untested cigarette for transport toward, past and beyond the testing station.

The frame or housing in which the conveyor 1 is rotatably mounted includes a stationary shoe or valve plate 21 which is outwardly adjacent to and abuts against the exposed end face of the flange 12. The shoe 21 has a nipple 22 which is connected with a source 27 of compressed testing fluid by a conduit 26. The discharge end of the nipple 22 communicates with a bore 23 which is machined into the valve plate 21 and which further communicates with a groove 24 provided in that end face of the valve plate 21 which abuts against the adjacent end face of the flange 12 so that the groove 24 communicates with successive sockets 19 of the flange 12 when the conveyor 1 rotates to advance successive cigarettes 3 toward, past and beyond the testing station. The groove 24 further communicates with a transducer 31 by way of a bore 28, which is machined into the valve plate 21, and a conduit 29. The transducer 31 can constitute a conventional electro-pneumatic transducer which converts pneumatic signals into corresponding electric signals. Such signals are thereupon processed and utilized for segregation of defective cigarettes 3 from satisfactory cigarettes in a manner not forming part of the present invention. For example, each such signal can be compared with a reference signal which is indicative of a satisfactory cigarette; when the difference between the signal which is generated by the transducer 31 and the reference signal exceeds a certain value, the corresponding cigarette is considered to be defective and is segregated from satisfactory cigarettes.

The left-hand flange 9 of the conveyor 1 is adjacent to a second stationary valve plate or shoe 32 having a groove 33 machined into that end face thereof which abuts against the conveyor 1. The groove 33 communicates with successive bores 11 of the flange 9 when the conveyor 1 is in rotary motion. This groove is connected with a second outlet of the source 27 of compressed testing fluid by a second conduit 36 through the medium of an injector nozzle 37 and a hollow cylindrical element 43 defining a chamber 38 which is in communication with the groove 33 of the valve plate 32 by an intercepting orifice 34. The cylindrical element 43 is formed with an annulus of venting openings 39 which connect the chamber 38 with the surrounding atmosphere. The injector nozzle 37 comprises a conically converging inlet portion 41 and a cylindrical flow restricting portion 42 defining a channel having a diameter which is less than the diameter of the chamber 38 and matches the diameter at the discharge end of the passage in the inlet portion 41.

Figure 2:
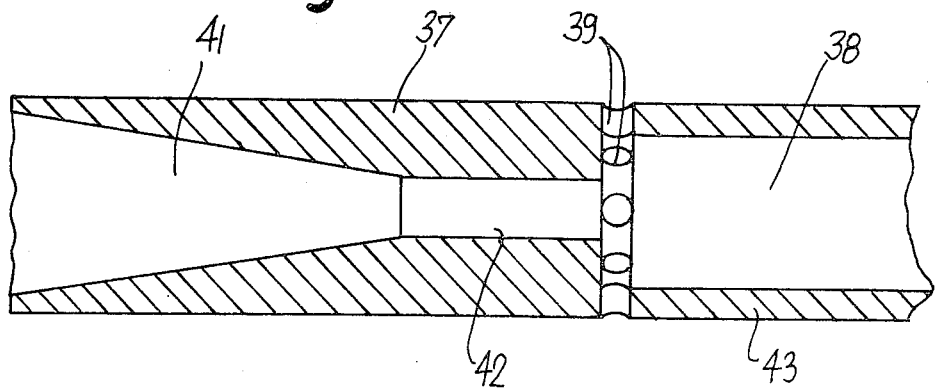
FIG. 2 an enlarged view of a detail in the upper left-hand portion of FIG. 1.

The mode of operation of the testing apparatus which is shown in FIGS. 1 and 2 is as follows:

It is assumed that the wrapper of the cigarette 3 which is shown in FIG. 1 is provided with a set of venting holes or pores which are supposed to permit a certain flow of cool atmospheric air into the interior of the cigarette to mix with the column of hot tobacco smoke when the cigarette is lighted. The conveyor 1 is in motion, and successive flutes 2 receive filter cigarettes 3 of unit length at the upstream side of the testing station shown in FIG. 1. Each cigarette 3 is inserted into the respective flute 2 while the corresponding sealing nipple 14 is retracted (for example, by a stationary cam) against the opposition of the corresponding coil spring 13 so that the space between the flange 9 and the retracted nipple 14 suffices for convenient insertion of an untested cigarette into the respective flute 2. The cam thereupon permits the coil spring 13 to expand and to move the end face 18 of the nipple 14 against the respective end of the cigarette 3 which is attracted to the conveyor 1 by suction in the ports 6 extending into the projections 4. The coil spring 13 thereby pushes the cigarette 3 against the flange 9 so that the left-hand end of the cigarette communicates with the bore 11 in the flange 9 while the right-hand end of such cigarette communicates with the passage 17 of the nipple 14. The conveyor 1 receives filter cigarettes 3 of unit length at the rate at which such cigarettes are formed in the filter tipping machine.

A properly inserted cigarette 3 assumes the position which is shown in FIG. 1 not later than when the corresponding flute 2 reaches the testing station between the groove 33 of the stationary valve plate 32 and the groove 24 of the stationary valve plate 21.

When the cigarette 3 arrives at the testing station, the bores 11 and 17 begin to communicate with the respective grooves 24 and 33 so that streams of compressed testing fluid flow from the respective conduits 26, 36 into the corresponding ends of the wrapper of the cigarette 3 at the testing station. The conduit 26 admits testing fluid into the nipple 22 whereby such fluid flows through the bore 23 and into the groove 24 whence the fluid flows into the socket 19 and thence into the passage or bore 17 when the corresponding nipple 14 reaches the testing station. The conduit 36 continuously admits testing fluid into the groove 33 whence the fluid flows into the left-hand end of the cigarette 3 when such cigarette reaches the testing station because the corresponding bore 11 then communicates with the groove 33.

Since the speed of the conveyor 1 in a modern filter tipping machine is extremely high (as mentioned above, such machines can turn out well in excess of one-hundred filter cigarettes per second), the testing fluid is abruptly admitted into both ends of the wrapper of the cigarette 3 which reaches the testing station. Consequently, the pressure of testing fluid in the conduits 26 and 36 drops drastically when some of the testing fluid is permitted to flow into the interior of the wrapper of the cigarette 3 at the testing station. Such rapid drop of pressure of the testing fluid normally results in oscillations of the columns of air in the conuits 26, 36 as well as in the conduit 29 which latter connects the groove 24 with the transducer 31. Consequently, and in order to ensure that the signal which is generated by the transducer 31 during passage of a cigarette 3 through the testing station will be a reliable indicator of the condition of the respective cigarette (namely, of the permeability of the wrapper to atmospheric air which is to flow into the column of hot tobacco smoke when the cigarette is lighted), it is desirable to await the termination or dying out of oscillations of the column or columns of air in the aforementioned conduits 26, 36 and 29. This can take up a reasonably long interval of time, namely, a substantial part of that interval which is allotted for the testing of successive cigarettes 3 at the testing station. As mentioned before, these intervals are extremely short (normally in the range of a few milliseconds) so that any shortening of such intervals for the purpose of preventing oscillations of the air column or columns from influencing the quality of the testing operation could adversely affect the testing operation. In other words, postponements of the generation of testing signals until after the oscillations of the air columns have faded out in conventional testing apparatus greatly reduce the length of those intervals which remain available for the actual testing operation.

It has been found that the arrangement which is shown in the left-hand portion of FIG. 1 and, on a larger scale, in FIG. 2 of the drawing is capable of effectively eliminating or greatly reducing the extent and duration of oscillations of air columns in various conduits, particularly in the conduit 36 which connects the source 27 of compressed testing fluid with the groove 33 of the stationary valve plate 32. This arrangement, designated by the reference charecter 44, includes the aforementioned injector nozzle 37 and the parts which define the chamber 38 and the intercepting orifice 34 leading from the chamber 38 into the groove 33 of the stationary valve plate 32. The stream of testing fluid which issues from the source 27 and flows through the conduit 36 enters the conically converging inlet portion 41 of the injector nozzle 37 on its way into and through the cylindrical flow restricting portion 42 before entering the larger-diameter chamber 38. The provision of the cylindrical portion 42, whose inner diameter is a relatively small fraction of the diameter of the chamber 38, ensures that the flow of testing fluid entering the chamber 38 is laminar. Furthermore, such flow is without any turbulence. The length of the conical inlet portion 41 and of the cylindrical portion 42 of the injector nozzle 37 can be readily selected in such a way that the turbulence at the outlet of the nozzle 37 is negligible or non-existent. Consequently, the air stream which leaves the cylindrical portion 42 of the injector nozzle 37 constitutes a strongly coherent laminar jet of gaseous fluid which passes, without any guidance, through the chamber 38 to enter the groove 33 via orifice 34. The inlet of the orifice 34 is in register with the passage of the cylindrical portion 42 of the injector nozzle 37. This ensures that the entire laminar and turbulence-free jet of testing fluid enters the orifice 34 on its way into the groove 33 of the stationary valve plate 32. Such testing fluid then enters the corresponding end of the cigarette 3 as soon as the respective bore 11 of the flange 9 reaches the testing station.

The other end of the wrapper of the cigarette 3 at the testing station simultaneously receives a stream of testing fluid via conduit 26, nipple 22, bore 23, groove 24, socket 19 and passage 17. This marks the beginning of the testing operation. During testing, the pressure of testing fluid in the groove 24 (such pressure changes abruptly when the ends of the wrapper at the testing station begin to communicate with the grooves 24 and 33) is communicated to the transducer 31 via conduit 29 whereby the transducer generates a signal which is indicative of the condition of ventillating pores or holes in the wrapper of the cigarette 3. If desired, an in order to further improve the result of the testing operation, the transducer 31 can be mounted directly in or on the valve plate 21.

The pressure in the grooves 24 and 33 again changes abruptly as soon as a cigarette 3 advances beyond the testing station, namely, as soon as the bores 11 and 19 move out of register with the corresponding grooves 24 and 33. Such abrupt changes of pressure in the grooves 24 and 33 can again cause oscillations of the columns of air in the conduits 26, 36 and 29. The oscillations are effectively reduced or eliminated by the provision of the arrangement 44 including the injector nozzle 37 and the parts defining the chamber 38 and orifice 34. It has been found that such arrangement reliably reduces the oscillations, or eliminates such oscillations altogether, so that the entire or substantially entire interval of travel of a cigarette 3 through the testing station can be used for ascertainment of the condition of the wrapper of such cigarette. It has also been found, that the arrangement 44 prevents oscillations of the column of air in the conduit 36 even when the conveyor 1 is driven at a high or very high speed, such as is required in the aforediscussed modern high-speed filter tipping or analogous machines. Consequently, the signals which are generated by the transducer 31 are not influenced by oscillations of the air column in the conduit 36 because such oscillations cannot develop at all or are negligible. Moreover, and as already mentioned above, the absence of oscillations renders it possible to utilize the entire interval of travel of a cigarette 3 through the testing station for the generation of a reliable signal which is thereupon processed and used to expel or segregate defective cigarettes from satisfactory cigarettes on their way toward the next processing station, e.g., during travel of filter cigarettes from the filter tipping to the packing machine. It will be readily appreciated that the reliability of the transducer 31 and of the entire testing apparatus is greatly increased in the entire intervals of travel of cigarettes through the testing station can be used for generation of appropriate test signals.

As mentioned above, the arrangement 44 is installed between the source 27 of compressed testing fluid and the left-hand groove 33 of FIG. 1, namely between the conduit 36 and the valve plate 32. It goes without saying that this apparatus can comprise a second oscillation eliminating or preventing arrangement which is installed (at 144) between the conduit 26 and the groove 24, as well as an additional arrangement which can be installed (at 244) between the groove 24 and the transducer 31. This further reduces the likelihood of adverse influence of oscillations of columns of testing fluid in response to rapid changes in pressure of such fluid as a result of abrupt arrival of cigarettes at and abrupt departure of cigarettes from the testing station.

As also mentioned above, the improved testing apparatus can be used with advantage in filter tipping machines, namely, in machines wherein plain cigarettes, cigarillos or cigars are united with filter mouthpieces to form filter cigarettes, cigars or cigarillos of unit length or multiple unit length. Of course, such testing apparatus can be used with equal or similar advantage in other types of tobacco processing and analogous machines, for example, in machines for the production of plain cigarettes. Furthermore, the testing apparatus need not be utilized exclusively for detection of the condition of so-called aerating zones in the filter mouthpieces or tobacco containing portions of filter cigarettes or the like. Such testing apparatus are equally useful for detection of open seams, frayed ends of and/or holes in the wrappers of plain cigarettes, cigars, cigarillos or filter rod sections. In fact, the improved testing apparatus can be utilized in all such machines wherein the frequency of testing is sufficiently high to cause undesirable oscillations of the column or columns of testing fluid as a result of abrupt delivery of articles to and abrupt transport of articles from and beyond the testing station.

There is no need to guide the laminar air jet on its way through the chamber 38 of the oscillation-eliminating arrangement 44. Such laminar flow is sufficiently coherent to ensure that it passes through the chamber 38 and enters the groove 33 of the valve plate 32 by way of the orifice 34. The entire arrangement 44 can be mounted directly on the stationary valve plate 32 or on another portion of the means for supporting the rotary conveyor 1.

It is believed that free transfer of testing fluid in the form of a coherent laminar flow from the injector nozzle 37, through the chamber 38, and into the orifice 34 (such orifice can form part of a transducer which replaces the transducer 31) is the reason for elimination or reduction of intensity of oscillations of the column of testing fluid in the conduit 36. The conicity of the passage in the inlet portion 41 of the injector nozzle 37 contributes to the formation of a highly desirable coherent laminar flow of air which advances into and through the chamber 38 wherein the pressure matches atmospheric pressure.

Another important advantage of the improved testing apparatus is that it allows for further increase of the frequency at which the cigarettes are tested, for example, by reducing the available intervals of time for each testing operation. This is desirable and advantageous in connection with further development of presently known filter tipping and similar machines wherein the trend continues to be toward higher output, i.e., toward an output which is even in excess of the presently available outputs. Still another advantage of the improved testing apparatus is that the elimination of oscillations of the column of testing fluid in the conduit 36 (and in the other conduits if such conduits are also equipped with the improved oscillation eliminating arrangement) is achieved in an extremely simple and inexpensive way. The provision of injector nozzle 37 and of means defining the chamber 38 and orifice 34 constitutes a negigible expense when compared with the cost of a modern, high-speed filter tipping or like machine. Furthermore, such arrangement is extremely reliable and requires little or no attention so that it can be utilized for long periods of time without requiring cleaning, inspection or replacement. The bulk of the improved testing apparatus does not exceed the bulk of conventional testing apparatus so that the improved apparatus can be readily installed in existing filter tipping or like machines as a superior substitute for conventional testing apparatus.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for testing at a testing station the open-ended tubular wrappers of cigarettes or analogous rod-shaped articles wherein the wrapper surrounds a filler of tobacco and/or filter material, comprising conveyor means arranged to transport a succession of articles toward, past and beyond the testing station; means for admitting a stream of gaseous testing fluid into at least one end of the wrapper forming part of the article advancing past the testing station with attendant establishment of a pressure differential between the interior and the exterior of the wrapper, including a source of gaseous testing fluid, conduit means for conveying a stream of testing fluid from said source toward the testing station, and means for preventing oscillations of testing fluid in said conduit means as a result of abrupt admission and/or abrupt termination of admission of testing fluid into the wrappers of articles at the testing station, said oscillation preventing means comprising an injector nozzle receiving the stream of testing fluid from said conduit means and arranged to convert such stream into a coherent flow, means defining an intercepting orifice located in the path of said coherent flow and arranged to convey such flow to the testing station, and means defining a chamber which communicates with the atmosphere and through which the coherent flow advances with clearance on its way from said nozzle toward and into said orifice; and signal generating means for monitoring said pressure differential.

2. The apparatus of claim 1, wherein the diameter of said chamber exceeds the diameter of said orifice.

3. The apparatus of claim 2, wherein said nozzle defines a passage having an outlet end whose diameter is less than the diameter of said chamber.

4. The apparatus of claim 1, wherein said orifice defining means includes a stationary valve member adjacent to one end of the wrapper at the testing station and including means for admitting testing fluid into such end of the wrapper during travel of the respective article past the testing station.

5. The apparatus of claim 4, wherein said nozzle amd said chamber defining means are mounted on said valve member.

6. The apparatus of claim 1, wherein said nozzle defines a passage having an inlet portion whose diameter decreases in a direction from said conduit means toward said chamber.

7. The apparatus of claim 1, wherein said nozzle defines a passage for testing fluid, the length of said passage between said conduit means and said chamber being such that the stream is converted into a laminar flow.

8. The apparatus of claim 1, further comprising second conduit means receiving a stream of testing fluid from said source and arranged to convey such fluid toward the other end of each wrapper at the testing station, and second oscillation preventing means interposed between said second conduit means and the testing station.

9. The apparatus of claim 1, further comprising additional conduit means arranged to convey testing fluid between the interior of a wrapper at the testing station and said monitoring means, and additional oscillation preventing means communicating with said additional conduit means.

10. The apparatus of claim 1, wherein the testing fluid is air.

11. The apparatus of claim 1, wherein said nozzle is coaxial with said chamber and with said orifice.

* * * * *